United States Patent
Baba et al.

(10) Patent No.: US 6,531,521 B2
(45) Date of Patent: Mar. 11, 2003

(54) METHOD OF PRESERVING PHOTOSENSITIVE COMPOSITION

(75) Inventors: Koji Baba, Toyonaka (JP); Toshiya Inoue, Toyonaka (JP); Shigeo Hozumi, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/835,337

(22) Filed: Apr. 17, 2001

(65) Prior Publication Data
US 2002/0025992 A1 Feb. 28, 2002

(30) Foreign Application Priority Data
Apr. 18, 2000 (JP) ........................................ 2000-116228

(51) Int. Cl.$^7$ .................................................. C08F 2/46
(52) U.S. Cl. ................... 522/6; 522/1; 522/90; 522/96; 522/100; 522/101; 522/103; 522/104; 522/149; 522/150; 522/151; 522/152; 522/153; 522/154; 522/182; 528/502 R; 528/502 C; 53/428
(58) Field of Search ................ 522/1, 6, 149, 522/150, 151, 152, 153, 154, 90, 96, 100, 101, 103, 104, 182; 528/502 C, 502 R; 53/428

(56) References Cited

U.S. PATENT DOCUMENTS

| | | | | | |
|---|---|---|---|---|---|
| 3,850,675 A | * | 11/1974 | Miller | ......................... | 427/493 |
| 4,096,323 A | * | 6/1978 | Wegemund et al. | ........ | 526/219 |
| 4,107,386 A | * | 8/1978 | Gruber et al. | ............... | 428/412 |
| 4,126,737 A | * | 11/1978 | Gruber et al. | ............... | 526/217 |
| 4,172,951 A | * | 10/1979 | Gruber et al. | ............... | 526/282 |
| 4,263,397 A | * | 4/1981 | Horikoshi et al. | ........... | 430/496 |
| 4,420,330 A | * | 12/1983 | Jakusch et al. | .............. | 148/105 |
| 4,689,086 A | * | 8/1987 | Naumann et al. | ........... | 524/431 |
| 4,814,260 A | * | 3/1989 | Koboshi et al. | ............. | 430/264 |
| 5,239,016 A | * | 8/1993 | Cochran et al. | ....... | 252/188.28 |
| 5,429,920 A | * | 7/1995 | Hioki et al. | ................. | 430/577 |

FOREIGN PATENT DOCUMENTS

| | | |
|---|---|---|
| JP | 9-204052 A | 8/1997 |
| JP | 2000-98606 A | 4/2000 |

OTHER PUBLICATIONS

N.S. Allen, "Photopolymerisation and Photoimaging Science and Technology", pp. 40–44. (1989).
J.M. Sturge, Neblette's Handbook of Photography and Reprography, Materials, Processes and Systems, 7$^{th}$ Edition, (1977), pp. 435–436.

* cited by examiner

Primary Examiner—James J. Seidleck
Assistant Examiner—Sanza L. McClendon
(74) Attorney, Agent, or Firm—Birch, Stewart, Kolasch & Birch, LLP

(57) ABSTRACT

A practically excellent method for preserving a photosensitive composition Containing a photopolymerization initiator and a photopolymerizable monomer and/or oligomer, which comprises placing and preserving the photosensitive composition in a light shielding vessel, wherein the product of the void ratio (%) in the vessel and the oxygen partial pressure (hPa) in the void part is 1500 (%·hPa) or more is provided; and the method imparts remarkably improved preservation stability.

6 Claims, No Drawings

METHOD OF PRESERVING PHOTOSENSITIVE COMPOSITION

BACKGROUND OF THE INVENTION

The present invention relates to a method of preserving a photosensitive composition, such as a photosensitive resin composition suitable for a resist and the like used for producing a color filter used in a color liquid crystal display apparatus, image element and the like, Conventionally, a photosensitive composition is placed and preserved in a light shielding vessel such as a brown glass bottle and the like. However, change of the viscosity by time of the photosensitive composition, generation of aggregations and the like are sometimes caused, during the preservation thereof in a shielding vessel. Such change of the viscosity and generation of aggregations often stop the coating line of this composition.

The present inventors have intensively studied for improving preservation stability of a photosensitive composition in view of such problems. As the result, they have found that preservation stability of the photosensitive composition can be improved remarkably by controlling the void ratio and oxygen partial pressure in a vessel filled with this composition. Thus, the present invention was completed.

SUMMARY OF THE INVENTION

The present invention provides a practically excellent method for preserving a photosensitive composition containing a photopolymerization initiator and a photopolymerizable monomer and/or oligomer, which comprises placing the photosensitive composition in a vessel, wherein the product of the void ratio (%) in the vessel and the oxygen partial pressure (hpa) in the void part is 1500 (%·hPa) or more.

DETAILED DESCRIPTION OF THE PREFERRED EMBODIMENTS

The photosensitive composition of the present invention contains a photopolymerization initiator and at least one selected from photopolymerizable monomers and photopolymerizable oligomers. As the photopolymerization initiator, one which is usually used in this field may be used. Examples thereof include acetophenone-based initiators, benzoin-based initiators, benzophenone-based initiators, thioxanetone-based initiators, triazine-based initiators, and other initiators.

Specific examples of the acetophenone-based photopolymerization initiator include oligomers of diethoxyacetophenone, 2-hydroxy-2-methyl-1-phenylpropan-1-one, benzyldimethylketal, 2-hydroxy-2-methyl-1-[4-(2-hydroxyethoxy)phenyl]propan-1-one, 1-hydroxycyclohexylphenylketone, 2-methyl-2-morpholino-1-(4-methylthiophenyl)propan-1-one, 2-benzyl-2-dimethylamino-1-(4-morpholinophenyl)butan-1-one or 2-hydroxy-2-methyl-1-[4-(1-methylvinyl)phenyl]propan-1-one.

Specific examples of the benzoin-based photopolymerization initiator include benzoin, benzoin methyl ether, benzoin ethyl ether, benzoin isopropyl ether, benzoin isobutyl ether, and the like.

Specific examples of the benzophenone-based photopolymerization initiator include benzophenone, methyl o-benzoylbenzoate, 4-phenylbenzophenone, 4-benzoyl-4'-methyldiphenyl sulfide, 3,3',4,4'-tetra(tert-butyl peroxycarbonyl)benzophenone, 2,4,6-trimethylbenzophenone.

Specific examples of the thioxanetone-based photopolymerization initiator include 2-isopropylthioxanetone, 4-isopropylthioxanetone, 2,4-diethylthioxanetone, 2,4-dichlorothioxanetone, 1-chloro-4-propoxythioxanetone, and the like.

Specific examples of the triazine-based photopolymerization initiator include 2,4-bis(trichloromethyl)-6-(4-methoxyphenyl)-1,3,5-triazine, 2,4-bis(trichloromethyl)-6-(4-methoxynaphthyl)-1,3,5-triazine, 2,4-bis(trichloromethyl)-6-piperonyl-1,3,5-triazine, 2,4-bis(trichloromethyl)-6-(4-methoxystyryl)-1,3,5-triazine, 2,4-bis(trichloromethyl)-6-[2-(5-methylfuran-2-yl)ethenyl]-1,3,5-triazine, 2,4-bis(trichloromethyl)-6-[2-(furan-2-yl)ethenyl]-1,3,5-triazine, 2,4-bis(trichloromethyl)-6-[2-(4-diethylamino-2-methylphe nyl)ethenyl]-1,3,5-triazine, 2,4-bis(trichloromethyl)-6-[2-(3,4-dimethoxyphenyl)ethenyl]-1,3,5-triazine, and the like.

Specific examples of the other photopolymerization initiator include 2,4,6-trimethylbenzoyldiphenylphosphine oxide, 2,2'-bis(o-chlorophenyl)-4.4',5,5'-tetraphenyl -1,2'-biimidazole, 10-butyl-2-chloroacridone, 2-ethylanthraquinone, benzyl, 9,10-phenanthrenequinone, camphorquinone, methyl phenylglyoxylate, titanocene compounds, and the like. These photopolymerization initiators can also be used alone or in combination of two or more.

In the present invention, a photoinitiation assistant can also be used in combination with a photopolymerization initiator. As the photoinitiation assistant, amine-based photoinitiation assistants and alkoxyanthracene-based photoinitiation assistants are exemplified.

Specific examples thereof include triethanolamine, methyldiethanolamine, triisopropanolamine, methyl 4-dimethylaminobenzoate, ethyl 4-dimethylaminobenzoate, isoamyl 4-dimethylaminobenzoate, 2-dimethylaminoethyl benzoate, 2-ethylhexyl 4-dimethylaminobenzoate, N,N-dimethyl p-toluidine, 4,4'-bis (dimethylamino) benzophenone (common name: Michler's ketone), 4,4'-bis (diethylamino)benzophenone, 9,10-dimethoxyanthracene, 2-ethyl-9,10-dimethoxyanthracene, 9,10-diethoxyanthracene, 2-ethyl-9,10-diethoxyanthracene and the like- These photoinitiation assistants can also be used alone or in combination of two or more of them Total amount of the photopolymerization initiators and photoinitiation assistants in the photosensitive composition of the present invention is generally from 3 to 30 parts by weight, preferably from 5 to 25 parts by weight, based on 100 parts by weight of the total solid content (excluding a solvent when used).

The photopolymerizable monomer and/or oligomer is a compound which causes polymerization by action of light and a photopolymerization initiator. In general, compounds having a polymerizable carbon-carbon unsaturated bond are examples thereof.

This photopolymerizable monomer can be selected from bi-functional monomers and other poly-functional monomers, in addition to mono-functional monomers. Specific examples of the mono-functional monomer include nonylphenylcarbitol acrylate, 2-hydroxy-3-phenoxypropyl acrylate, 2-ethylhexylcarbitol acrylate, 2-hydroxyethyl acrylate, N-vinylpyrrolidone and the like. Specific examples of the bi-functional monomer include 1,6-hexanediol di(meth)acrylate, ethyleneglycol di(meth)acrylate, neopentylglycol di(meth)acrylate, triethyleneglycol di(meth)acrylate, bis(acryloyloxyethyl) ether of bisphenol A, 3-methylpentanediol di(meth)acrylate, tricyclodecanedimethanol di(meth)acrylate and the like.

Specific examples of the other poly-functional monomer include trimethylolpropane tri(meth)acrylate, pentaerythritol tri(meth)acrylate, pentaerythritol tetra(meth)acrylate, dipentaerythriol penta(meth)acrylate, dipentaerythriol hexa(meth)acrylate, tris(methacryloyloxyethyl) isocyanurate and the like. The photopolymerizable monomers can also be used alone or in combination of two or more, The photopolymerizable oligomer can be selected from oligomers having an acryloyl group, methacryloyl group, vinyl group or the like. Specifically, urethane acrylates such as urethane acrylate and urethane methacrylate, epoxy acrylates such as epoxy acrylate and epoxy methacrylate, polyester acrylates such as polyester acrylate and polyester methacrylate, melamine acrylates such as melamine acrylate and melamine methacrylate, acrylic resin acrylates, unsaturated polyesters, polyenes and the like are exemplified Examples of the urethane acrylates include those obtained by reacting an organic polyisocyanate, a polyol and a hydroxyacrylate-based compound, and those obtained by reacting an organic polyisocyanate and a hydroxyacrylate-based compound.

Examples of the epoxyacrylates include those obtained by reacting an acrylic acid and/or a methacrylic acid with an epoxy resin such as a bisphenol A type epoxy resin or a novolak type epoxy resin. Examples of the polyester acrylates include those obtained by reacting an acrylic acid and/or a methacrylic acid with a polyester polyol synthesized from a poly-hydric alcohol and a poly-valent carboxylic acid.

Examples of the melamine acrylates include those obtained by de-alcohol reaction of a β-hydroxyethyl acrylate with a melamine resin obtained by polycondensation of melamine, urea, benzoquamine and the like with formalin. Examples of the acrylic resin acrylates include those obtained by reacting an acrylic acid and/or a methacrylic acid with a functional group, such as a carboxylic group, hydroxyl group, glycidyl group and the like, contained in an acrylic resin.

Examples of the unsaturated polyesters include those obtained by reacting a polyol with an α, β-unsaturated dicarboxylic acid such as fumaric acid, maleic anhydride and the like. Examples of the polyenes include those obtained by reacting allyl alcohol, vinyl alcohol and the like with an organic polyisocyanates. The photopolymerizable oligomers can also be used alone or in combination of two or more.

The photopolymerizable monomer and/or oligomer is contained in an amount in the range from 5 to 90% by weight based on the total weight of solid components in the photosensitive composition.

The photosensitive composition of the present invention can further comprise coloring materials, binder resins, fillers, other polymer compounds, surfactants (pigment dispersing agents, antistatic agents), adherence promoters, antioxidants, ultraviolet absorbers, aggregation inhibitors, solvents, leveling agents, neutralizers, coloration improving agents and the like, if required.

As the coloring material, usually, inorganic or organic coloring matters are used. As the inorganic coloring matter, metal compounds such as metal oxides and metal complex salts are listed. Specifically, metal oxides or metal oxide composites such as iron, cobalt, nickel, aluminum, cadmium, lead, copper, titanium, magnesium, chromium, zinc, antimony and the like are listed. As the organic coloring matter, specifically, compounds described in Color Index (published by The Society of Dyers and Colorists) are listed. These coloring matters can be used alone or in combination of two or more. More specific examples thereof include compounds represented by the following Color Index (C.I.) numbers.

C.I. Acid Red 73,

C.I. Direct Red 1, 23, 89,

C.I. Acid Orange 7, 8, 28, 56, 88, 140,

C.I. Pigment Yellow 20, 24, 31, 53, 83, 86, 93, 94, 109, 110, 117, 125, 137, 138, 139, 147, 148, 150, 152, 153, 154, 155, 166, 173, 180 and 185, C.I. Pigment Orange 13, 31, 36, 38, 40, 42, 43, 51, 55, 59, 61, 64, 65 and 71, C.I. Pigment Red 9, 97, 105. 122, 123, 144, 149, 166, 168, 176, 177, 180, 192, 215, 216, 224, 242 and 254, C.I. Pigment Violet 14, 19, 23, 29, 32, 33, 36, 37 and 38, C.I. Pigment Blue 15 (C.I. Pigment Blue 15.3, 15:4, 15:6 and the like), 21, 22, 28, 60 and 64, C.I. Pigment Green 7, 10, 15, 25, 36 and 47, C.I. Pigment Brown 28, C.I. Pigment Black 1 and 7, and the like.

When a coloring material is contained, the amount of the coloring material is usually from about 3 to 70% by weight based on the total solid content.

As the binder resin, homopolymers or copolymers of one or more compounds having a polymerizable carbon-carbon unsaturated bond are exemplified, Examples of the compound having a polymerizable carbon-carbon unsaturated bond include aromatic vinyl compounds such as styrene, α-methylstyrene and vinyltoluene, unsaturated alkyl carboxylates such as methyl (meth)acrylate, ethyl (meth)acrylate, butyl (meth)acrylate, 2-hydroxyethyl (meth)acrylate and benzyl (meth)acrylate, unsaturated aminoalkyl carboxylates such as aminoethyl acrylate, unsaturated glycidyl carboxylates such as glycidyl (meth)acrylate, vinyl carboxylates such as vinyl acetate and vinyl propionate, vinyl cyanide compounds such as (meth)acrylonitrile and α-chloroacrylonitrile, unsaturated carboxylic acids such as (meth)acrylic acid, crotonic acid, itaconic acid, maleic acid and fumaric acid, etc.

When a binder resin is contained, the amount of the binder resin is usually from about 5 to 70% by weight based on the total solid content.

As the filler, glass, silica, alumina and the like are specifically listed. As the other polymer compound, polyvinyl alcohol, polyacrylic acid, polyethylene glycol monoalkyl ether, polyfluoroalkyl acrylate and the like are specifically listed. As the surfactant (pigment dispersing agent, antistatic agent), various nonionic, cationic or anionic surfactants can be used. As adherence promoter, vinyltrimethoxysilane, vinyltriethoxysilane, vinyltris(2-methoxyethoxy)silane, N-(2-aminoethyl)-3-aminopropylmethyldimethoxysilane, N-(2-aminoethyl)-3-aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloyloxypropyltrimethoxysilane, 3-mercaptopropyltrimethoxysilane and the like are specifically listed.

As the antioxidant, 2,2'-thiobis(4-methyl-6-t-butylphenol), 2,6-di-t-butyl-4-methylphenol and the like are specifically listed As the ultraviolet absorber, 2 -(3-t-butyl-5-methyl-2-hydroxyphenyl)-5-chlorobenzotriaz ole, alkoxybenzophenone and the like are specifically listed. As the aggregation inhibitor, sodium polyacrylate and the like are specifically listed. As the solvent, esters such as methyl acetate, ethyl acetate, propyl acetate, isopropyl acetate, butyl acetate, isobutyl acetate, methyl propionate, ethyl propionate, propyl propionate, butyl propionate, ethyl pyruvate, methyl 3-methoxypropionate and ethyl 3-ethoxypropionate; ketones such as acetone, methyl ethyl ketone, methyl amyl ketone, diisobutyl ketone, cyclopentanone and cyclohexanone; glycol ether esters such as 3-methoxy butyl acetate and propylene glycol monomethyl ether acetate; aromatic hydrocarbons such as benzene, toluene, o-, m- or p-xylene, are specifically listed.

Further, as the leveling agent, straight silicone oils such as dimethyl silicone oil, methylphenyl silicone oil and methylhydrogen silicone oil; organo-modified silicone oils such as methylphenyl silicone oil, alkyl-modified silicone oil, fluorine-modified silicone oil, polyether-modified silicone oil, alcohol-modified silicone oil, amino-modified silicone oil and epoxy-modified silicone oil: perfluoro group-containing polymers; salts of perfluoroalkyl carboxylates; and the like are listed. As the neutralizer. calcium stearate, hydrotalcite and the like are listed. As the coloration improving agent, 9,10-dihydro-9-oxa-10-phosphophenanethrene-10-oxide and the like are listed.

After dissolving and dispersing various components uniformly, the photosensitive composition of the present invention is placed in a vessel made of glass, plastic, metal and the like, and preserved in the vessel closely plugged. Preferably, the vessel is a light-shielding vessel, or the vessel is placed in a light-shielded place.

In the present invention, it is preserved under the conditions wherein the product of the void ratio (%) in the vessel and the oxygen partial pressure (hPa) in the void part is 1500 (%·hPa) or more. Preferably, the product is 2000 (%·hPa) or more.

The void ratio (%) means the ratio, represented by percentage, of the volume of the void in the vessel to the inner volume of the vessel. The volume of the void is obtained by subtracting the volume of the composition to be preserved from the inner volume of the vessel.

Lower preservation temperature is preferable.

The following examples will further illustrate the present invention in detail, but do not limit the scope of the present invention. In the examples, % and parts representing content in a composition and use amount are by weight, and % representing void ratio after filling a vessel with a composition is by volume.

PREPARATION EXAMPLE

As the coloring material, photopolymerizable monomer, photopolymerization initiator and solvent, the following components were used to prepare a composition in a compounding ratio shown in Table 1.

Coloring Material

A pigment dispersion prepared by mixing C.I. Pigment Green 36/C.I. Pigment Yellow 150/dispersing agent/ propylene glycol monomethyl ether acetate in a weight ratio of 9.75/5.25/5.1/79.9.

Photopolymerizable Monomer

Dipentaerythritol hexaacrylate

Photopolymerization Initiator

Irgacure 369; 2-benzyl-2-dimethylamino-1-(4-morpholinophenyl)butan-1-one [manufactured by Chiba Specialty Chemicals Co., Ltd.]

TAZ-PP: 2,4-bis(trichloromethyl)-6-piperonyl-1,3,5-triazine [available from Nippon Sievel Hegunner Co., Ltd.]

Binder Resin 34.8% propylene glycol monomethyl ether acetate solution of methacrylic acid/benzyl methacrylate copolymer= 35/65 (molar ratio, weight-average molecular weight: 29,200)

Solvent

Propylene glycol monomethyl ether acetate

TABLE 1

| <Compounding ratio> | |
|---|---|
| Coloring material (amount of dispersion) | 43.46 parts |
| Photopolymerizable monomer | 4.85 parts |
| Photopolymerization initiator: | |
| Irgacure 369 | 0.87 parts |
| TAZ-PP | 0.68 parts |
| Binder resin (amount of solution) | 13.94 parts |
| Solvent | 36.20 parts |

Example 1

Under an air atmosphere of an oxygen partial pressure of 204 hPa, the above-mentioned composition was placed and sealed in a brown clear glass bottle (light shielded) so that the void ratio was 10%, then, preserved In a light shielded incubator controlled at 40° C. Ten days after, the glass bottle was removed from the incubator, and the solution in the bottle was observed to recognize that the initial condition was maintained without increase in viscosity and generation of an aggregate.

Example 2

The composition was placed in the sealed bottle and preserved according to the same manner as in Example 1 except that the void ratio was changed to 15%. Ten days after, the solution in the bottle was observed to recognize that the initial condition was maintained without increase in viscosity and generation of an aggregate.

Example 3

A photosensitive composition was prepared without using a coloring material in the compounding example in Table 1, This composition was placed in the sealed bottle and preserved according to the same manner as in Example 1. Ten days after, the solution in the bottle was observed to recognize that the initial condition was maintained without increase in viscosity and generation of an aggregate.

Comparative Example 1

The composition was placed in the sealed bottle and preserved according to the same manner as in Example 1 except that the void ratio was changed to 5%. Ten days after, the solution in the bottle was observed to recognize increase in viscosity and generation of an aggregate.

Comparative Example 2

The composition was preserved according to the same manner as in Example 1 except the composition was placed in the sealed bottle under a nitrogen atmosphere instead of an air atmosphere in Example 1. Two days after, the solution in the bottle was observed to recognize increase in viscosity and generation of an aggregate.

TABLE 2

| | Void ratio | Oxygen partial pressure (hPa) | Void ratio × oxygen partial pressure (% hPa) | Preservation stability * |
|---|---|---|---|---|
| Example 1 | 10 | 204 | 2040 | ○ |
| Example 2 | 15 | 204 | 3060 | ○ |
| Example 3 | 10 | 204 | 2040 | ○ |
| Comparative example 1 | 5 | 204 | 1020 | X |
| Comparative example 2 | 10 | 0 | 0 | X |

\* ○ indicates good Preservation stability.
X indicates poor Preservation stability.

According to the present invention, change of the viscosity by time of the photosensitive composition, generation of aggregations and the like can be prevented. That is, preservation stability can be improved remarkably by controlling the void ratio and oxygen partial pressure in a vessel filled with the composition. By this method, cost of production of a photosensitive composition can be reduced. Also, users of this composition can reduce receiving inspection frequency and can make the production scheme efficiently, leading to possibility of cost reduction.

What is claimed is:

1. A method for preserving a photosensitive composition containing a photopolymerization initiator and a photopolymerizable monomer and/or oligomer, which comprises placing the photosensitive composition in a vessel, wherein the product of the void ratio (%) in the vessel and the oxygen partial pressure (hPa) in the void part is 1500 (%·hPa) or more.

2. The method for preserving a photosensitive composition according to claim 1, wherein the product of the void ratio (%) in the vessel and the oxygen partial pressure (hPa) in the void part is 2000 (%·hPa) or more.

3. The method for preserving a photosensitive composition according to claim 1, wherein the vessel is a light-shielding vessel.

4. The method for preserving a photosensitive composition according to claim 1, wherein the photopolymerization initiator is triazine-based photopolymerization initiator.

5. The method for preserving a photosensitive composition according to claim 1, which further comprises a coloring material.

6. A method for producing a photosensitive composition comprising a photopolymerization initiator and a photopolymerizable monomer and/or oligomer which comprises a step of preserving the photosensitive composition in a light shielding vessel, wherein the product of the void ratio (%) in the vessel and the oxygen partial pressure (hPa) in the void part is 1500 (%·hPa) or more.

\* \* \* \* \*